(12) United States Patent
Vartiainen et al.

(10) Patent No.: US 9,668,924 B2
(45) Date of Patent: Jun. 6, 2017

(54) METHOD OF SECURING CONDUCTIVE THREAD IN AN ABSORBENT ARTICLE

(71) Applicant: SCA Hygiene Products AB, Göteborg (SE)

(72) Inventors: Kent Vartiainen, Lerum (SE); Mattias Bosaeus, Kållered (SE); Allan Elfström, Deptford, NJ (US)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 14/777,532

(22) PCT Filed: Mar. 19, 2013

(86) PCT No.: PCT/EP2013/055687
§ 371 (c)(1),
(2) Date: Sep. 16, 2015

(87) PCT Pub. No.: WO2014/146694
PCT Pub. Date: Sep. 25, 2014

(65) Prior Publication Data
US 2016/0051416 A1    Feb. 25, 2016

(51) Int. Cl.
*A61F 13/42* (2006.01)
*A61F 13/15* (2006.01)

(52) U.S. Cl.
CPC ........ *A61F 13/42* (2013.01); *A61F 13/15585* (2013.01); *A61F 2013/424* (2013.01);
(Continued)

(58) Field of Classification Search
CPC ............... Y10T 56/1056; Y10T 56/108; Y10T 56/1304; Y10T 15/1309; A61F 13/42; A61F 13/44; A61F 2013/424; A61F 2013/423; A61F 2013/427; A61F 2013/15585; A61F 2013/15121; A61F 2013/1513; A61F 2013/15146; A61F 2013/15154; A61F 2013/1517; A61F 2013/15918; A61F 2013/1591
(Continued)

(56) References Cited

U.S. PATENT DOCUMENTS 2,372,632 A * 3/1945 Webb ............... A41D 27/24
156/152
2,727,295 A * 12/1955 Wright ............... A47G 27/045
112/432
(Continued)

FOREIGN PATENT DOCUMENTS

WO    WO-96/14813 A1    5/1996
WO    WO-00/00144 A2    1/2000
(Continued)

*Primary Examiner* — Linda L Gray
(74) *Attorney, Agent, or Firm* — Drinker Biddle & Reath LLP (57) ABSTRACT

A method of securing a conductive thread in an absorbent article is disclosed. The method includes: passing a thread through a first surface of the absorbent article; and anchoring a first length of the thread on the first surface by applying adhesive at a position on the first length of the thread between a point at which the thread passes through the surface and a first end of the thread to cover at least a portion of the thread and a portion of the surface.

12 Claims, 10 Drawing Sheets

(52) U.S. Cl.
CPC ...... *Y10T 156/108* (2015.01); *Y10T 156/1056* (2015.01); *Y10T 156/1304* (2015.01); *Y10T 156/1309* (2015.01)

(58) Field of Classification Search
USPC .......................................................... 156/93
See application file for complete search history.

(56) References Cited

U.S. PATENT DOCUMENTS

| | | |
|---|---|---|
| 4,356,818 A | 11/1982 | Macias et al. |
| 4,768,023 A | 8/1988 | Xie |
| 5,845,644 A | 12/1998 | Hughes et al. |
| 7,250,547 B1 | 7/2007 | Hofmeister et al. |
| 7,977,529 B2 | 7/2011 | Bergman et al. |
| 2005/0156744 A1 | 7/2005 | Pires |
| 2008/0243099 A1 | 10/2008 | Tippey et al. |
| 2009/0199753 A1* | 8/2009 | Niizeki ................. D05B 65/00 112/292 |
| 2011/0263952 A1 | 10/2011 | Bergman et al. |
| 2011/0295619 A1 | 12/2011 | Tough |
| 2013/0018231 A1* | 1/2013 | Hong ..................... A61F 13/42 600/300 |

FOREIGN PATENT DOCUMENTS

| | | |
|---|---|---|
| WO | WO-2004/100763 A2 | 11/2004 |
| WO | WO-2006/047815 A1 | 5/2006 |
| WO | WO-2011/054045 A1 | 5/2011 |
| WO | WO-2011/156862 A1 | 12/2011 |

\* cited by examiner

METHOD OF SECURING CONDUCTIVE THREAD IN AN ABSORBENT ARTICLE

CROSS-REFERENCE TO RELATED APPLICATION

This application is a §371 National Stage Application of PCT International Application No. PCT/EP2013/055687 filed Mar. 19, 2013, which is incorporated herein in its entirety.

TECHNICAL FIELD

The present disclosure relates to a method of securing a conductive thread to a surface in an absorbent article, and particularly a method of securing a conductive sensor element in an absorbent article such that it is at least partly in contact with an absorbent core of the absorbent article, for the purpose of sensing the presence of moisture or other parameters in the absorbent article.

BACKGROUND

Absorbent sanitary articles, such as diapers, sanitary towels, incontinence garments and the like, have widespread utility in both domestic and institutional settings for such purposes as the care of infants, the management of menstrual discharge, and the management of incontinence. However, a known problem associated with the use of absorbent sanitary articles is that the articles have a limited capacity for absorption, which, if exceeded, will cause the sanitary article to become ineffective, e.g. to leak or at least to fail to absorb further.

Therefore, users of such articles, or their carers, must predict when a sanitary absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Systems which are able to alert the user or carer to saturation or impending saturation of the absorbent article are therefore of benefit. Such systems may take the form of an absorbent article having embedded sensors which connect to a monitoring unit. The monitoring unit contains data processing electronics which is able to alert the user or carer by means of a visual or audible signal that the diaper is approaching saturation.

In some proposed arrangements, conductive elements are provided which extend from a monitoring module to an absorbent core of the absorbent article. To provide sensing capability, the conductive elements may be pairs of conductive wires terminating in uninsulated end portions, between which an electric circuit may be completed when moisture is present in the absorbent core. Alternatively or additionally to conductive wires having uninsulated end portions acting as moisture sensors, other sensors such as temperature, pH or glucose sensors may be provided at the end of conductive elements for assessing biometric or medical information of a user.

However, it is difficult to run conductive wires through an absorbent article to a monitoring unit, especially when there is a requirement for wires to be retained at specific locations within the article, for example to effect detection or sensing at particularly well-defined regions of the garment or to avoid short circuits being inadvertently created between close-running conductive elements.

SUMMARY

According to the present disclosure, there is provided a method of securing a conductive thread in an absorbent article, the method comprising: passing a thread through a first surface of the absorbent article; and anchoring a first length of the thread on the first surface by applying adhesive at a position on the first length of the thread between a point at which the thread passes through the surface and a first end of the thread to cover at least a portion of the thread and a portion of the surface.

In one embodiment, the adhesive is applied so as not to cover the first end of the thread, and wherein after the adhesive is applied, the thread is cut at a point between the first end and the adhesive.

In one embodiment, the thread is cut at a point at which the thread exits the adhesive between the adhesive and the first end.

In one embodiment, the adhesive is applied to cover a point at which the thread passes through the surface.

In one embodiment, the adhesive is provided by direct deposition to the surface.

In one embodiment, the adhesive is provided on the surface of an adhesive tape which is applied to the surface.

In one embodiment, the adhesive tape is a double-sided adhesive tape having adhesive on both sides.

In one embodiment, the surface is a surface of a layer that covers an absorbent core of the article, and the thread passes through the absorbent core between a second end of the thread and a point at which the thread passes through the surface.

In one embodiment, the thread passes through the first surface a second time between the point at which the thread passes through the surface and the second end of the thread.

In one embodiment, the thread is anchored to the first surface between a point at which the thread passes through the first surface a second time and the second end of the thread.

In one embodiment, the second end of the thread is maintained in a fixed position relative to the absorbent article and tension is applied to the thread at the first end of the thread before, and optionally while, the first end of the thread is anchored.

In one embodiment, the first surface is covered by a second surface at least in a region where the thread runs along the first surface.

In one embodiment, the second surface is a surface of a nonwoven fabric.

In one embodiment, the first surface is a surface of a waterproof layer.

In one embodiment, the absorbent article is a diaper, the conductive thread is for sensing moisture in the diaper, and a second end of the thread is terminated for connection to a data logger.

BRIEF DESCRIPTION OF THE DRAWINGS

To better understand the present invention, and to show embodiments of the same, reference will now be made to the accompanying Drawings, in which.

DETAILED DESCRIPTION OF PARTICULAR EMBODIMENTS

Exemplary absorbent sanitary articles, manufactured during implementations of the present invention, will now be described. For simplicity, a diaper is used as one exemplary absorbent sanitary article, although the techniques of the present invention are applicable to other absorbent sanitary articles such as incontinence garments, sanitary towels, and medical dressings, as one skilled in the art will recognise.

An exemplary diaper, in common with many conventional absorbent sanitary articles, has an absorbent core placed proximate the body of a user, and covered by an impermeable backsheet. Liquid or semi-solid material arriving at the absorbent article from the user's body will thus be absorbed by the absorbent core but prevented from further permeating the impermeable backsheet. The absorbent article thus manages effectively the flow of liquid and semi-solid liquid from the user's body. The absorbent article may also be provided with a topsheet placed in between the absorbent core and the user's body on the side of the absorbent core opposite to the impermeable backsheet, the topsheet being permeable and serving to retain the absorbent core and/or provide comfort to the user. Such constructions are well known in the art, and the wide variation of types of such article will not be further described herein, although one skilled in the art will not have difficulty in applying the disclosed techniques to such articles as may be required.

In assembling an absorbent article intended to have conductive elements, such as conductive threads, for example for acting as sense wires for a monitoring system, the sense wires should extend to be in at least partial contact with the absorbent core, but also need to run in a well-defined route to the location of, for example, the monitoring unit or a terminal connector.

A method of manufacturing an absorbent article having conductive sensing elements and being a first implementation of an embodiment of the present invention is now described, with reference to FIGS. 1 to 5.

Figure 1:
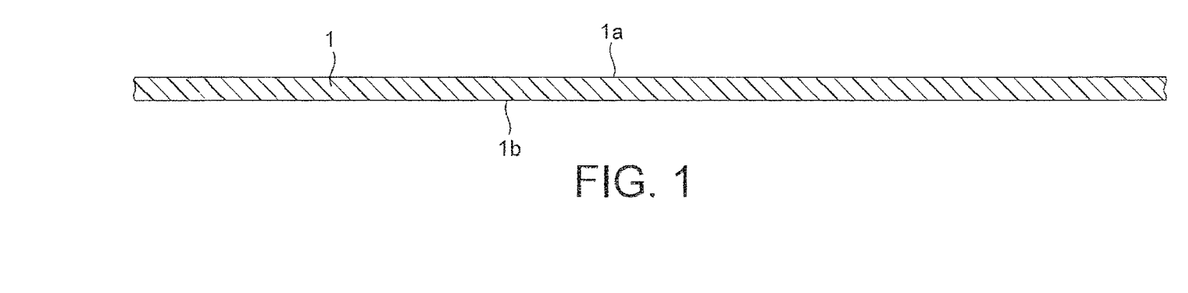
FIGS. 1 to 5 show a sequence of stages in a first implementation of an embodiment of the present invention.

In FIG. 1, an impermeable backsheet 1 is shown. The impermeable backsheet has a surface 1a which will, in use, face away from the body of the user and a surface 1b which will face the body of the user through the absorbent core. In the present implementation, the sensing elements are conductive threads which run along at least a portion of the absorbent core and terminate at the monitoring unit. However, to ensure that the threads are securely routed and neither become displaced nor contact one another, the threads are preferably made taut and confined to well-defined routes during the manufacturing process.

Figure 2:
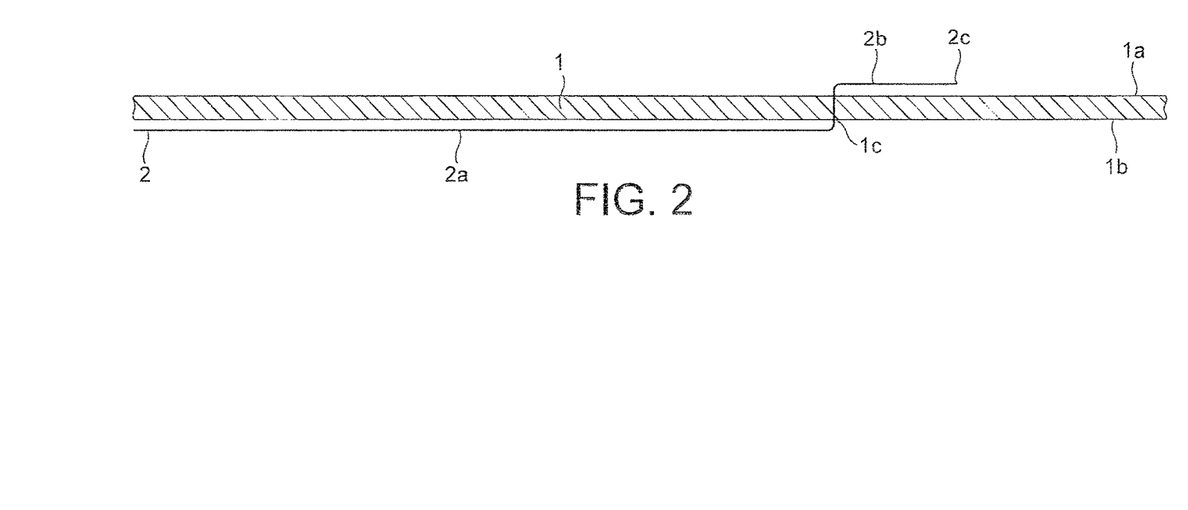

Hence, in FIG. 2, a thread 2 is routed along surface 1b of backsheet 1 as first length of thread 2a, traverses backsheet 1 via hole 1c to reach surface 1a, and extends along surface 1a as a second length 2b, terminating in first end 2c. Such a construction can easily be provided by straightforward sewing techniques.

To ensure that the thread is confined to its assigned route, and does not deviate either during manufacturing or use of the article, tension should be applied to thread 2 at a second end relative to first end 2c to pull the thread at least partially taut in its path to eliminate at least some of any residual slack when the second end of thread 2 is terminated at a connector or monitoring module. To enable this to be achieved, the thread should be anchored at the first end 2c before any tension is applied, otherwise the thread is likely to be displaced.

Figure 3:
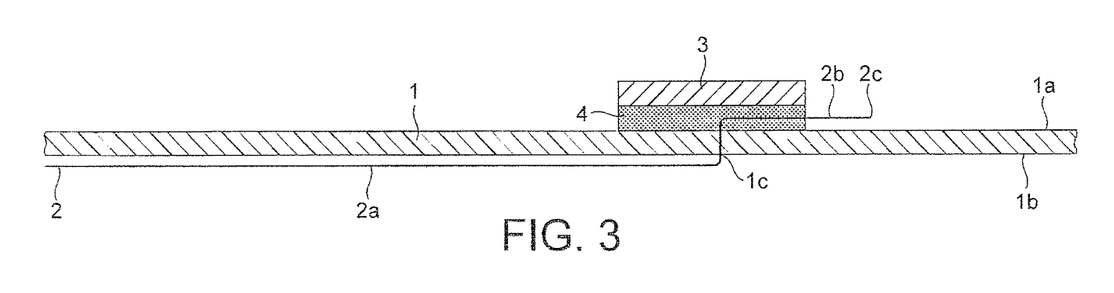

To achieve such anchoring, as shown in FIG. 3, adhesive 4 is applied to at least a portion of portion 2b of thread 2, covering also a portion of surface 1a. In FIG. 3, the adhesive 4 covers also the hole 1c at which thread 2 passes through backsheet 1 from surface 1b to surface 1a. This construction has an advantage that the waterproofing of backsheet 1 is assured. Adhesive 4 is provided on the surface of adhesive tape 3, which provides a substrate for supporting the adhesive 4, enabling easy and convenient application of the adhesive to thread 2 and backsheet 1. However, adhesive could instead be applied in another form, such as a liquid glue which cures to a solid, such as cyanoacrylate glue. Of course, if layer 1 is not waterproof, or if a further waterproof layer is provided to cover surface 1a of backsheet 1, covering hole 1c with adhesive 4 is not strictly necessary. Regardless of whether hole 1c is covered by the adhesive, thread length 2b is anchored by adhesive 4.

Figure 4:
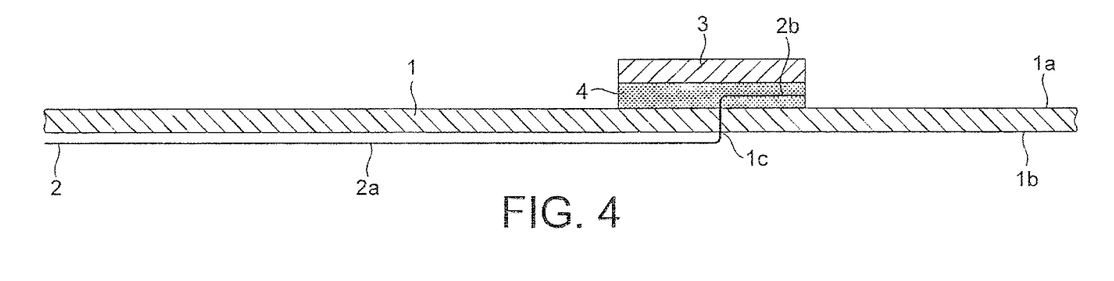

At the state shown in FIG. 3, end 2c of thread 2 protrudes from adhesive 4. The greater the proportion of thread 2 that protrudes from the adhesive, the greater the possibility of an accidental short circuit between the free end 2c of thread 2 and another conductive thread, where present. Further, moisture external to backsheet 1 could undesirably be sensed by end 2c of thread 2. Accordingly, end 2c may be cut from thread 2, such as close to or at a surface of adhesive layer 4, as shown in FIG. 4. In cutting the end of thread 2c from thread 2, a portion of the adhesive layer 4 and the adhesive tape 3 may also be removed to assure that the end of the thread is flush with the end of adhesive 4, although this is not essential. In such a flush or close-cut configuration, the thread end is surrounded by adhesive on all but an end surface. If tension is applied to thread 2 before the adhesive is set, it is also possible to withdraw end 2c of thread 2 to be flush with a surface of the adhesive or even fully enclose end 2c with adhesive.

Subsequently, absorbent core 5 is placed against surface 1b of backsheet 1 so that at least a portion of the absorbent core 5 is in contact with at least a portion of length 2a of thread 2. A topsheet 6, being liquid permeable, may then be placed on a body-facing side of absorbent core 5 for comfort, also shown in FIG. 5. However, provision of a topsheet is strictly optional, as one skilled in the art will appreciate.

Figure 5:
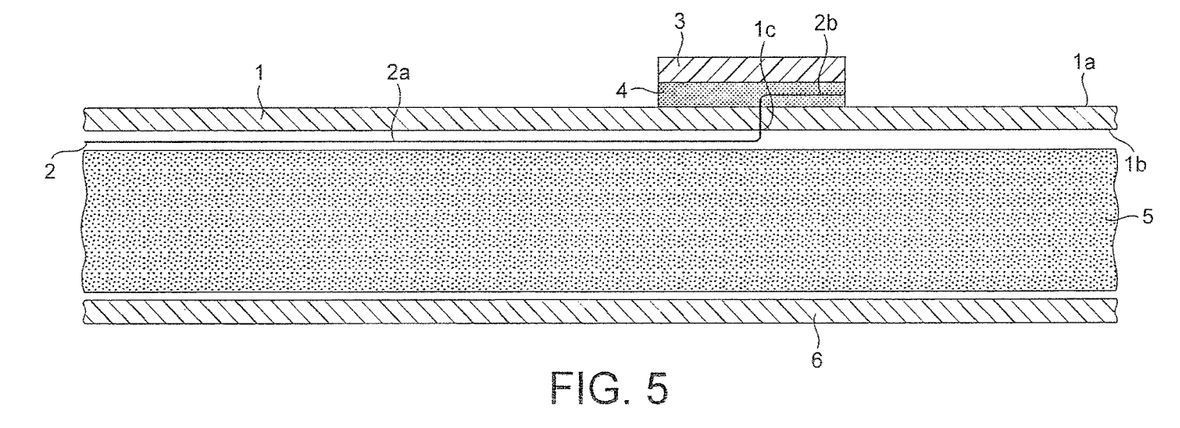

In the arrangement of FIG. 5, sufficient moisture penetrating absorbent core 5 will contact conductive thread 2, and have a possibility of completing a circuit with a second conductive thread sufficiently nearby. Alternatively, conductive thread 2 may be formed of two conductive elements spaced apart from one another and forming a circuit when moisture contacts the thread. The thread may be partially coated with an insulating coating, such as acrylic resin or adhesive tape, along a part of length 2a, such that only moisture extending to a predetermined exposed active portion of length 2a will be able to make conductive electrical contact with moisture in the absorbent core. Such a configuration is of particular use when it is desired only to detect moisture at particular locations in the absorptive core, or when a plurality of sensor elements are provided each detecting discrete locations.

Of course, the skilled reader will understand that layer 1 need not be an impermeable backsheet, and could be a permeable or semi-permeable backsheet, with a further impermeable outer sheet in contact with surface 1b, or with a further absorptive element or other layer between surface 1b and any impermeable layer. Such structures also fall within the scope of the present invention. Similarly, there is no restriction as such on the materials or properties of the absorptive core 5, and any absorptive core which may be known in the art may be used, without limitation, including cores utilising natural and/or man made fibres and/or superabsorbent polymers. As for conductive thread 2, presently silver-plated nylon is contemplated, although other conductive threads as may be known in the art may be used.

Figure 6:
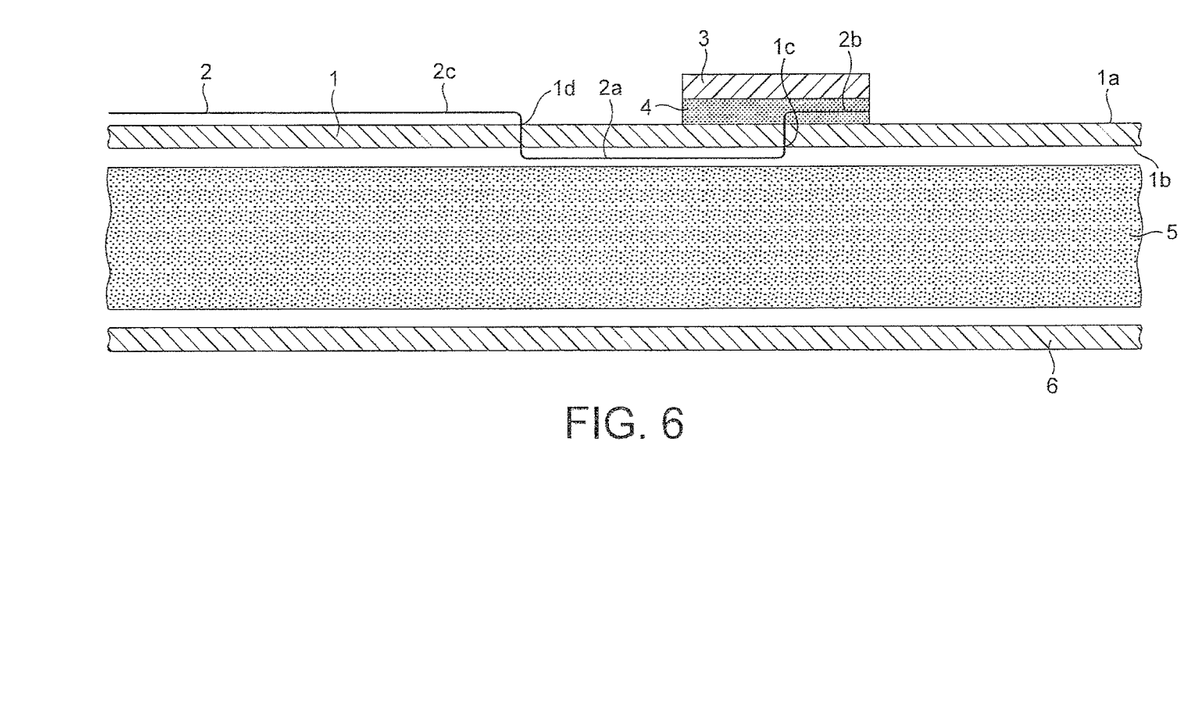
FIG. 6 shows the result of a modified implementation of an embodiment of the present invention.

As an alternative to, or in addition to partially coating length 2a of conductive thread 2, to restrict the regions of absorbent core 5 at which sensing may be achieved, or for convenience of attachment to a monitoring unit which may be positioned on side 1b of backsheet 1 opposite to the side facing the absorbent core, the thread may be brought again through the backsheet from surface 1b to surface 1a through second hole 1d, after travelling in contact with core 5 over length 2a, to run again along surface 1a of backsheet 1 as length 2c. Such is shown in FIG. 6. Indeed, the conductive thread may make multiple such transitions from surface 1b to surface 1a from first to second end. Such may be of particular use in defining a suitable two-dimensional path for conductive thread 2 from absorbent core to monitoring unit.

In a second implementation of an embodiment of the present invention, the core is assembled to the backsheet, with or without an optional topsheet, before the thread is run. The thread may then penetrate the core. Such may be seen in the sequence of FIGS. 7 to 10.

Figure 7:
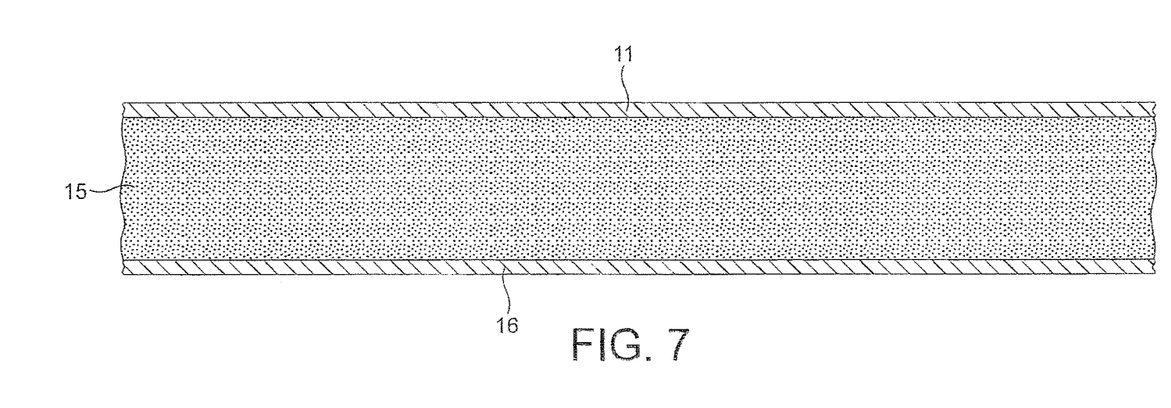
FIGS. 7 to 10 show a second implementation of an embodiment of the present invention.
Figure 8:
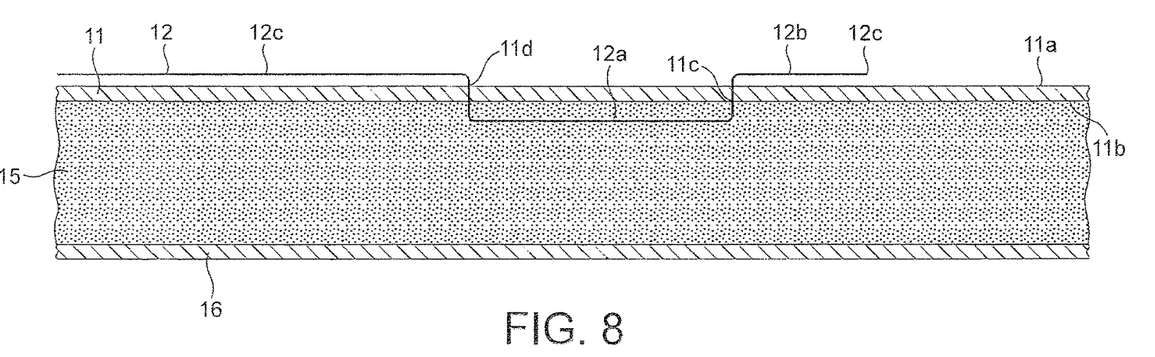

In FIG. 7, absorbent core 15 lies between backsheet 11 and topsheet 16. In FIG. 8, conductive thread 12 has been run along surface 11a of backsheet 11 with length 12c, penetrates backsheet 11 at second hole 11d to penetrate also absorbent core 15, runs within absorbent core 15 as length 12a, before again penetrating backsheet 11 from surface 11b to surface 11a through hole 11c. Conductive thread 12 then continues as length 12b towards end 12c. Accordingly, since conductive thread 12 penetrates absorbent core 15, the sensor can be more sensitive to moisture present in the absorbent core, and moisture need not penetrate the entire absorbent core from a side in contact with the body of a user before the sensor may be triggered. The depth of penetration of conductive thread 12 into absorbent core 15, as well as the length of thread 12 within absorbent core 15, may be selected to provide different reaction characteristics. For example, a thread which penetrates deeply into absorbent core 15 from surface 11b of backsheet 11 so as to run relatively closely to the user may react more rapidly to an influx of liquid, but may also react more readily to transient moisture or sweat.

Figure 9:
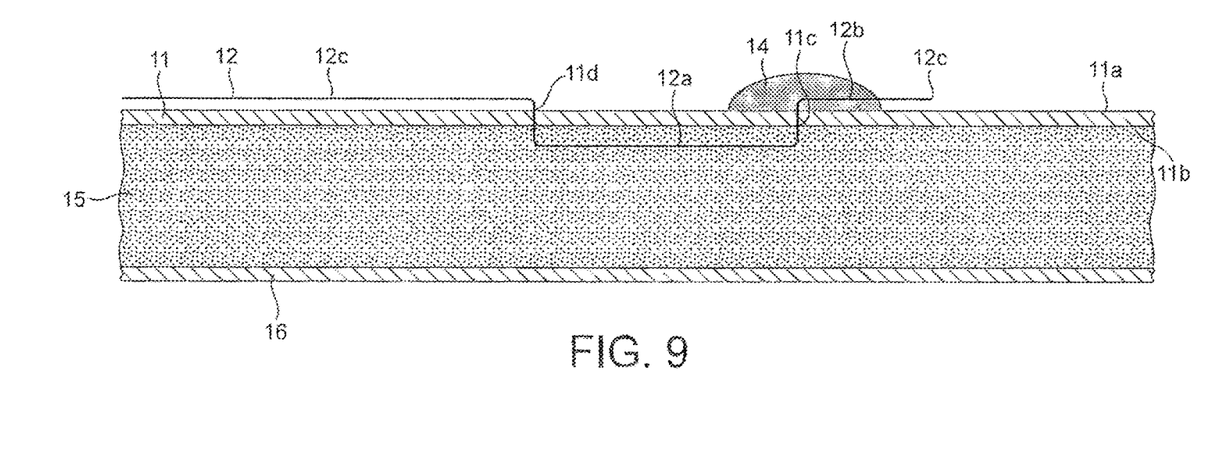

In FIG. 9, adhesive 14 has been applied, for example as a liquid adhesive which cures to a solid, such as cyanoacrylate glue, to length 12b of conductive thread 12 to cover at least a portion of surface 11a. Alternatively, an adhesive tape may be used as described in the earlier embodiment. Adhesive 14 also covers hole 11c to retain the waterproofing of backsheet 11.

Figure 10:
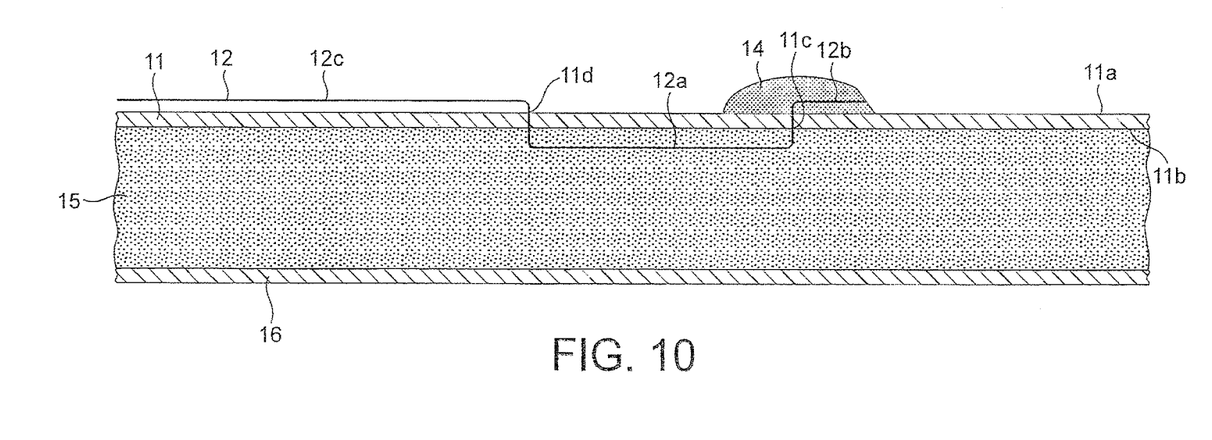

As for the previous implementation, end 12c of thread 12 is cut away, such as flush with adhesive 14. As previously mentioned, a particularly simple way to achieve this, as shown in FIG. 10, is to cut the adhesive as well as the thread such that a portion of the adhesive present on surface 11a of backsheet 11, as well as end 12c of thread 12, is removed.

Whether or not sheet 11, or indeed sheet 1 in the first implementation is permeable or impermeable, a second, outer layer may be provided to cover any threads running along surface 11a of backsheet 11 to protect the threads from displacement and, if necessary, to provide a further impermeable layer. Such a configuration is shown in FIG. 11.

Figure 11:
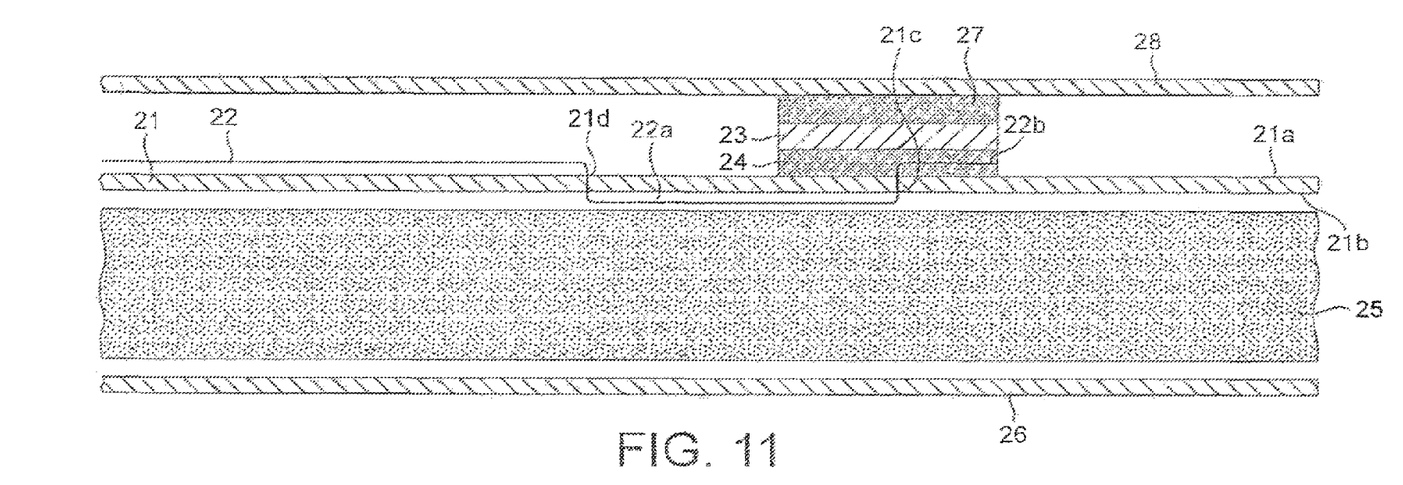
FIG. 11 shows a modification of the second implementation of an embodiment of the present invention.

In FIG. 11, absorbent core 25 is positioned between topsheet 26 and backsheet 21, and thread 22 is run along surface 21a of backsheet 21. Thread 22 penetrates backsheet 21 at second hole 21d, runs along surface 21b of backsheet 21 along length 22a, penetrates backsheet 21 again at hole 21c, and is anchored at length 22b using adhesive 24 supported on adhesive tape 23. Alternatively, as for the earlier embodiments, the thread 22 may penetrate absorbent core 25, and the adhesive may be provided as a liquid adhesive which cures to a solid. However, in the embodiment of FIG. 11, adhesive tape 23 is a double-sided adhesive tape, having a second layer of adhesive 27 on a surface of adhesive tape 23 opposed to the surface supporting adhesive 24. Such adhesive may be used to provide support for an impermeable outer sheet 28, which may be, for example, a non-woven fabric. Equally, a region of glue provided as described with regard to FIG. 9 could be used to both anchor thread 22 and/or secure outer sheet 28 in situ.

Once one end of the conductive thread is anchored so that the thread runs, at least partially, along or within the absorbent core, the thread may be routed to a monitoring unit provided on the absorbent article, or nearby. An exemplary configuration of such an absorbent article, in the form of a diaper having conductive sense threads and a monitoring unit, is shown in FIG. 12.

Figure 12:
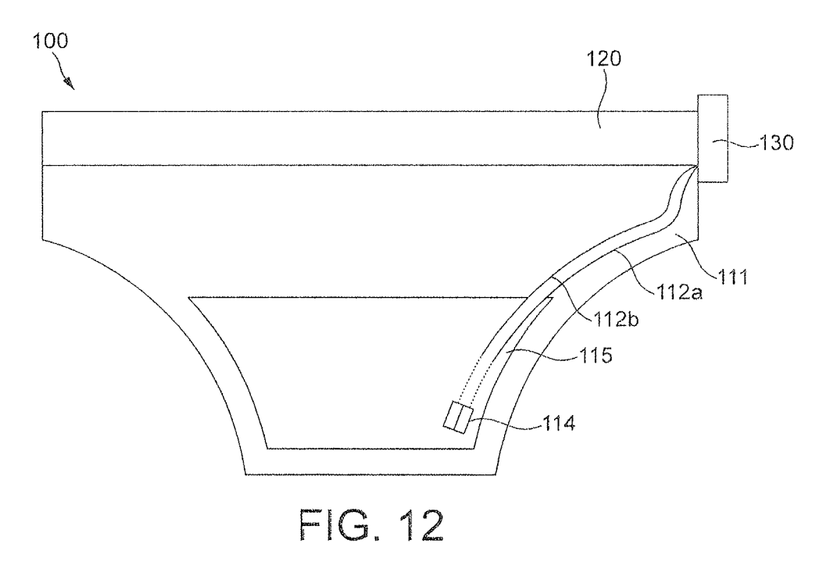
FIG. 12 shows an absorbent article in accordance with an embodiment of the present invention.

In FIG. 12, diaper 100 has waistband 120 and impermeable backsheet 111, and retains absorbent core 115 in a crotch position. Attached to a waistband 120 of the diaper 100 is an electronics unit 130, which has data processing electronics configured to sound an alert signal, which may be audible or visible, for example via a buzzer or an LED, once a circuit is completed between two contacts provided in or on a surface of the monitoring unit. Sense elements 112a and 112b are each connected to a terminal of monitoring unit 130, and together run in parallel along impermeable backsheet 111 on an outer side as far as a portion of backsheet 111 that overlies absorbent core 115. Each sense element 112a, 112b penetrates the backsheet 111, runs along or within the absorbent core 115, and then traverses backsheet 111 a second time to be anchored at adhesive 114. In use, moisture present in absorbent core 115 closes the circuit between sense elements 112a and 112b, and enables the monitoring unit 130 to react with the alert signal. Of course, other actions are possible with the monitoring unit on receiving appropriate sensor signals, and a data transmission could be initiated to a remote monitoring station, or event data could be recorded in a memory provided to the monitoring unit for later analysis.

The arrangement of FIG. 12 is purely exemplary, and equivalent configurations may be provided by any of the implementations described above or modifications thereof as may occur to one skilled in the art, taking into account his own knowledge and particular design requirements.

Particularly, in some circumstances, the conductive threads may be provided already attached to a connector frame or terminal block, or may be intended to be first attached to the absorbent article at the second end before the threads are run or anchored at the first end. In such circumstances, it may be desired for the thread to be run from the second end (connector end) to the first end (sensing end) and then, with the second end being anchored or held in a fixed position relative to the absorbent article, tension may be applied at the first end. In such a circumstance, the anchoring of the thread near the first end at a point apart from that end advantageously leaves sufficient length of thread between the anchor point and the first end to be gripped, thereby to apply and maintain tension to the thread during the anchoring process.

Further, any of the features described above may be provided in combination or separately and elements from one implementation may be applied without limitation in other implementations, for similar or distinct technical effects, as one skilled in the art may understand.

Particularly, the present invention is not limited to diapers, but may be used with any form of sanitary absorbent article, any form of absorbent core, any form of sensing element, any form of anchoring adhesive, and any form of topsheet, backsheet, or outer sheet, as may be known in the art, without limitation. The process may be implemented by hand, or by machine. All such modifications are intended to be within the scope of the appended claims.

The invention claimed is:

1. A method of securing a conductive thread in an absorbent article, the method comprising:
    passing the conductive thread through a first surface of the absorbent article;
    anchoring a first length of the conductive thread on the first surface by applying adhesive at a position on the first length of the conductive thread between a point at which the conductive thread passes through the first surface and a first end of the conductive thread to cover at least a portion of the conductive thread and a portion of the first surface, wherein the adhesive does not cover the first end of the conductive thread;
    subsequent to applying the adhesive, maintaining a second end of the conductive thread in a fixed position relative to the absorbent article and applying tension to the conductive thread at the first end of the conductive thread; and
    cutting the conductive thread at a point between the first end and the adhesive, and
    wherein the conductive thread passes through the first surface a second time between the point at which the conductive thread passes through the first surface and the second end of the conductive thread.

2. The method according to claim 1, wherein the conductive thread is cut at a point at which the conductive thread exits the adhesive between the adhesive and the first end.

3. The method according to claim 1, wherein the adhesive is applied to cover a point at which the conductive thread passes through the first surface.

4. The method according to claim 1, wherein the adhesive is provided by direct deposition to the first surface.

5. The method according to claim 1, wherein the adhesive is provided on the first surface of an adhesive tape which is applied to the first surface.

6. The method according to claim 5, wherein the adhesive tape is a double-sided adhesive tape having adhesive on both sides.

7. The method according to claim 1, wherein the first surface is a surface of a layer that covers an absorbent core of the article, and the conductive thread passes through the absorbent core between a second end of the conductive thread and a point at which the conductive thread passes through the first surface.

8. The method according to claim 1, wherein the conductive thread is anchored to the first surface between a point at which the conductive thread passes through the first surface a second time and the second end of the conductive thread.

9. The method according to claim 1, wherein the first surface is covered by a second surface at least in a region where the conductive thread runs along the first surface.

10. The method according to claim 9, wherein the second surface is a surface of a nonwoven fabric.

11. The method according to claim 1, wherein the first surface is a surface of a waterproof layer.

12. The method according to claim 1, wherein the absorbent article is a diaper, the conductive thread is for sensing moisture in the diaper, and a second end of the thread is terminated for connection to a data logger.

\* \* \* \* \*